(12) United States Patent
Munnich et al.

(10) Patent No.: US 8,097,287 B2
(45) Date of Patent: Jan. 17, 2012

(54) **USE OF A *GINKGO BILOBA* EXTRACT FOR THE TREATMENT OF MITOCHONDRIAL DISEASE OF GENETIC ORIGIN**

(75) Inventors: Arnold Munnich, Paris (FR); François Clostre, Paris (FR); Mehemed Ouzid, Ezanville (FR)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 36 days.

(21) Appl. No.: 12/375,213

(22) PCT Filed: Jul. 26, 2007

(86) PCT No.: PCT/FR2007/001286
§ 371 (c)(1),
(2), (4) Date: Mar. 19, 2009

(87) PCT Pub. No.: WO2008/012439
PCT Pub. Date: Jan. 31, 2008

(65) Prior Publication Data
US 2009/0258095 A1    Oct. 15, 2009

(30) Foreign Application Priority Data
Jul. 27, 2006  (FR) ..................................... 06 06862

(51) Int. Cl.
*A61K 36/16* (2006.01)

(52) U.S. Cl. ........................................................ 424/752
(58) Field of Classification Search .................. None
See application file for complete search history.

(56) References Cited

U.S. PATENT DOCUMENTS

2004/0109907 A1 * 6/2004 Teng .............................. 424/752
2005/0065099 A1 * 3/2005 Walkinshaw et al. .......... 514/27

FOREIGN PATENT DOCUMENTS

| FR | 2782008 | 2/2000 |
| WO | WO 98/51291 | 11/1998 |
| WO | WO 99/64028 | 12/1999 |
| WO | WO 03/047511 A2 | 6/2003 |

OTHER PUBLICATIONS

Bridi (Phytotherapy Research (2001), vol. 15, pp. 449-451).*
International Search Report for PCT/FR2007/001286 (WO 2008/012439 A3).
Written Opinion for PCT/FR2007/001286.
DiMauro, S. et al., "Mitochondrial Encephalomyopathies: An Update," Neuromuscular Disorders, Pergamon Press, GB, vol. 15, No. 4, pp. 276-286, Apr. 2005.
Muller, W.E. et al., "Stabilization of mitochondrial membrane potential by *Ginkgo biloba* extract EGb 761 (R)." Society for Neuroscience Abstract Viewer and Itinerary Planner, vol. 2003, p. 240.8, XP009079975.

* cited by examiner

*Primary Examiner* — Susan Hoffman
(74) *Attorney, Agent, or Firm* — Hunton & Williams LLP

(57) ABSTRACT

The invention relates to the use of *Ginkgo biloba* for the treatment of mitochondrial diseases of genetic origin and more particularly mitochondrial encephalomyopathies.

17 Claims, No Drawings

USE OF A *GINKGO BILOBA* EXTRACT FOR THE TREATMENT OF MITOCHONDRIAL DISEASE OF GENETIC ORIGIN

CROSS-REFERENCE TO RELATED APPLICATIONS

This application is the U.S. National Stage filing of International Application No. PCT/FR2007/001286, filed Jul. 26, 2007, which claims priority to French Patent Application No. 0606862, filed Jul. 27, 2006, the disclosures of which are hereby incorporated by reference.

The present Application relates to the use of a *Ginkgo biloba* extract for preparing a medicament intended to treat or prevent mitochondrial diseases of genetic origin.

The mitochondrial diseases are relatively frequent pathologies within the group of hereditary diseases of the metabolism. They are due to a dysfunction of the mitochondrial respiratory chain. Among the mitochondrial diseases, it is possible to distinguish those of genetic origin and in particular the mitochondrial encephalomyopathies which affect the muscle and nervous system and Leber's hereditary optic neuropathy. Among the mitochondrial encephalomyopathies, there can be mentioned the diseases linked to mitochondrial DNA anomalies such as MERRF syndrome (or Myoclonic Epilepsy associated with Ragged-Red Fibres), MELAS syndrome (or Mitochondrial Myopathy, Encephalopathy, Lactic Acidosis and Stroke-like episodes), Kearns-Sayre syndrome and Leigh's syndrome; there can also be mentioned the diseases due to anomalies of the nuclear genome including various forms of Leigh's syndrome and diseases dues to anomalies of other genes of the mitochondrial proteins such as hereditary spastic paraplegia and Friedreich's ataxia (Ann Pathol 2005, 25, 282-291).

For the treatment of these mitochondrial diseases of genetic origin, certain therapeutic agents have been clinically tested such as the quinone derivatives (ubiquinone, idebenone), dichloroacetate and metabolic supplements (succinate, creatine, carnitine). But even though in certain cases improvements in the patient's pathological state have been noted, none of these treatments appears satisfactory.

A subject of the invention is therefore the use of a *Ginkgo biloba* extract for preparing a medicament intended to treat or prevent the mitochondrial encephalomyopathies.

Preferably, a subject of the invention is the use of a *Ginkgo biloba* extract for preparing a medicament intended to treat or prevent the mitochondrial encephalomyopathies linked to mitochondrial DNA anomalies. Very preferably, these mitochondrial encephalomyopathies are chosen from MERRF syndrome and MELAS syndrome, and in particular MELAS syndrome.

Preferably also, a subject of the invention is the use of a *Ginkgo biloba* extract for preparing a medicament intended to treat or prevent the mitochondrial encephalomyopathies linked to anomalies of other genes of the mitochondrial proteins. Very preferably, this mitochondrial encephalomyopathy is Friedreich's ataxia.

The *Gingko biloba* extracts which can be used according to the present invention are extracts comprising flavone-glycosides and/or one or more terpene lactones.

Preferably, the flavone-glycosides and/or the terpene-lactones are present at least at a level of 24% by weight and more preferably at least at a level of 30%.

Moreover, the proportion of alkylphenol-type compounds in the *Ginkgo biloba* extract used according to the invention is preferably less than 10 ppm, more preferably less than 5 ppm and still more preferably less than 1 ppm.

Preferably, a *Ginkgo biloba* extract according to the invention comprises 20 to 30% by weight of flavone-glycosides, 2.5 to 4.5% by weight of ginkgolides A, B, C and J (in total), 2 to 4% by weight of bilobalide, less than 10% by weight of proanthocyanidines and less than 10 ppm of alkylphenol-type compounds. Very preferably, the *Ginkgo biloba* extract comprises 22 to 26% by weight of flavone-glycosides, 2.5 to 4.5% by weight of ginkgolides A, B, C and J (in total), 2 to 4% by weight of bilobalide, less than 10% by weight of proanthocyanidines and less than 1 ppm of alkylphenol-type compounds. Such an extract can be prepared according to the extraction methods as described in the patent EP 431535. Very preferably, the *Ginkgo biloba* extract is the standardized extract EGb 7610 as defined in particular in *La Presse médicale* (K. Drieu, 31, 25 Sep. 1986, supplement devoted to *Ginkgo biloba* extract, 1455-1457).

Any polycyclic aromatic hydrocarbon content which could be present in one of the *Gingko biloba* extracts as defined above could be reduced by implementing for example a method such as that described in the application WO 2006/17170. Preferably, an extract as defined above contains less than $10^{-6}$ g of polycyclic aromatic hydrocarbons per kilogram (kg) of extract.

Preferably also, a *Ginkgo biloba* extract according to the invention comprises 18 to 30% by weight of flavone-glycosides and 34 to 46% by weight of terpene-lactones, and preferably 20 to 28% by weight of flavone-glycosides and 36 to 44% by weight of terpene-lactones.

Preferably also, a *Ginkgo biloba* extract according to the invention comprises approximately 52% by weight of flavone-glycosides and approximately 13% by weight of terpene-lactones.

Such extracts can be prepared according to the extraction methods as described in the patent EP 1379262.

Preferably also, a *Ginkgo biloba* extract according to the invention comprises 28 to 35% by weight of flavone-heterosides and less than 1% of terpene-lactones and, preferably, 28 to 32% by weight of flavone-glycosides and less than 0.5% by weight of terpene-lactones. Such extracts can be prepared according to the extraction methods as described in the patent EP 822825.

If appropriate, in the case of extracts comprising ginkgolides, the ginkgolide or ginkgolides can be wholly or partly replaced by their acetylated homologues, their alkoxylated homologues or their glycosylated homologues.

As examples of glycosylated homologues, there can be mentioned the compounds of general formula (I)

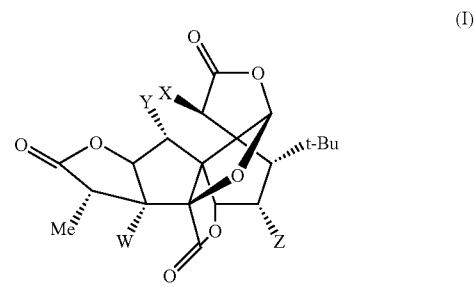

(I)

in which W, X, Y and Z represent independently the H, OH, linear or branched alkoxy or $O\text{-}G_s$ radicals, $G_s\text{-}OH$ representing a mono- or a disaccharide, or one of their derivatives or analogues, it being understood that at least one of W, X, Y or Z represents an O-$G_s$ radical. These compounds of general formula (I) are described in the patent application WO 98/52959.

The pharmaceutical compositions comprising a *Ginkgo biloba* extract can be in the form of solids, for example powders, granules, tablets, gelatin capsules, liposomes, suppositories or patches. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions comprising a *Ginkgo biloba* extract can also be presented in liquid form, for example, solutions, emulsions, suspensions or syrups. Appropriate liquid supports can be for example water, organic solvents such as glycerol or glycols, as well as their mixtures, in varying proportions, in water.

The administration of a medicament according to the invention can be carried out by topical, oral or parenteral route, or by injection (intramuscular, subcutaneous, intravenous etc.). Preferably, the *Ginkgo biloba* extract and in particular the standardized extract EGb 761 is administered by oral route.

The daily administration dose of *Ginkgo biloba* extract envisaged will depend on the concentration of active ingredients in the extract and the seriousness of the mitochondrial disease to be treated. In the particular case of the standardized extract EGb 761®, the latter can be administered at a daily dose comprised between 100 and 500 mg/day, preferably between 120 and 480 mg/day and very preferably between 240 and 480 mg/day.

Unless defined otherwise, all the technical and scientific terms used here have the same meaning as that usually understood by an ordinary specialist in the field to which this invention belongs.

Pharmacological Part

The activity of a *Ginkgo biloba* extract such as the extract EGb 761® in the treatment of the mitochondrial encephalomyopathies such as Friedreich's ataxia can be evaluated according to the following experimental protocol:

The study can be a phase II randomized, double-blind study, with two parallel arms versus placebo in child or adult patients, men or women, aged 13 years and more, and suffering from Friedreich's ataxia.

The extract EGb 761® could be administered in a dose of 120 mg twice daily.

During the study, imaging parameters are monitored using P-31 NMR spectroscopy. The clinical state is evaluated by seeking an improvement in symptoms of the disease on a clinical scale (ICARS), psychometric tests such as the "9 hole Peg test" and the patient's reaction time to a light stimulus "choice reaction time test". The criteria can be evaluated before and after 3 months of treatment.

The invention claimed is:

1. A method for the treatment mitochondrial encephalomyopathies linked to anomalies of the mitochondrial DNA or to anomalies of genes encoding mitochondrial proteins comprising administering to a patient in need thereof a therapeutically effective amount of a *Ginkgo biloba* extract.

2. The method of claim 1, wherein the mitochondrial encephalomyopathies are chosen from MELAS syndrome and MERRF syndrome.

3. The method of claim 1, wherein the mitochondrial encephalomyopathy is MELAS syndrome.

4. The method of claim 1, wherein the mitochondrial encephalomyopathy is Friedreich's ataxia.

5. The method of claim 1, wherein the extract comprises at least flavone-glycosides and/or terpene lactones.

6. The method of claim 1, wherein the extract comprises at least 24% by weight of flavone-glycosides and/or terpene lactones.

7. The method of claim 1, wherein the extract comprises less than 10 ppm of alkylphenol compounds.

8. The method of claim 1, wherein the *Ginkgo biloba* extract comprises 20 to 30% by weight of flavone-glycosides, 2.5 to 4.5% by weight of ginkgolides A, B, C and J, 2 to 4% by weight of bilobalide, less than 10% by weight of proanthocyanidines and less than 10 ppm of alkylphenol compounds.

9. The method of claim 8, wherein the *Ginkgo biloba* extract comprises 22 to 26% by weight of flavone-glycosides.

10. The method of claim 1, wherein the *Ginkgo biloba* extract is a standardized extract.

11. The method of claim 1, wherein the extract comprises less than 10–6 g of polycyclic aromatic hydrocarbons per kg of extract.

12. The method of claim 1, wherein the *Ginkgo biloba* extract comprises 18 to 30% by weight of flavone-glycosides and 34 to 46% by weight of terpene-lactones.

13. The method of claim 12, wherein the *Ginkgo biloba* extract comprises 20 to 28% by weight of flavone-glycosides and 36 to 44% by weight of terpene-lactones.

14. The method of claim 1, wherein the *Ginkgo biloba* extract comprises approximately 52% by weight of flavone-glycosides and approximately 13% by weight of terpene-lactones.

15. The method of claim 1, wherein the *Ginkgo biloba* extract comprises 28 to 35% by weight of flavone-glycosides and less than 1% of terpene-lactones.

16. The method of claim 15, wherein the *Ginkgo biloba* extract comprises 28 to 32% by weight of flavone-glycosides and less than 0.5% by weight of terpene-lactones.

17. The method of claim 6, wherein the extract comprises approximately 30% of flavone-glycosides and/or terpene lactones.

* * * * *